(12) United States Patent
Howard

(10) Patent No.: US 6,924,289 B2
(45) Date of Patent: Aug. 2, 2005

(54) BENZYL(IDENE)-LACTAM DERIVATIVES, THEIR PREPARATION AND THEIR USE AS SELECTIVE (ANT) AGONISTS OF 5-HT$_{1A}$- AND/OR 5-HT$_{1D}$ RECEPTORS

(75) Inventor: Harry R. Howard, Bristol, CT (US)

(73) Assignee: Pfizer Inc, New York, NY (US)

( * ) Notice: Subject to any disclaimer, the term of this patent is extended or adjusted under 35 U.S.C. 154(b) by 60 days.

(21) Appl. No.: 10/219,692

(22) Filed: Aug. 15, 2002

(65) Prior Publication Data

US 2003/0027812 A1 Feb. 6, 2003

Related U.S. Application Data

(62) Division of application No. 09/155,215, filed as application No. PCT/IB97/00076 on Feb. 3, 1997, now Pat. No. 6,462,048.
(60) Provisional application No. 60/015,134, filed on Mar. 29, 1996.

(51) Int. Cl.$^7$ ...................... A61K 31/496; C07D 401/10
(52) U.S. Cl. ............................. 514/253.03; 514/253.07; 514/253.12; 544/360; 544/363
(58) Field of Search ................................. 544/360, 363, 544/361; 514/253.12, 253.07, 253.03, 253.05

(56) References Cited

U.S. PATENT DOCUMENTS 6,467,084 B1 * 10/2002 Howard ................. 514/254.01

* cited by examiner

*Primary Examiner*—Emily Bernhardt
(74) *Attorney, Agent, or Firm*—A. David Joran

(57) ABSTRACT

The present invention relates to lactam derivatives of the formula

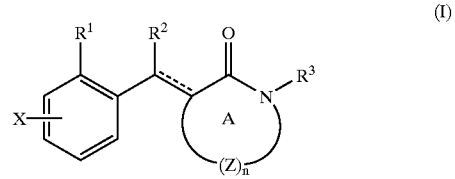

wherein $R^1$, $R^2$, $R^3$, A, X, Z, n and the dashed line are defined herein, and pharmaceutical compositions thereof, to processes and intermediates for their preparation, and to their medicinal use as selective agonists and antagonists of serotonin 1 (5-HT$_1$) receptors, specifically, of one or both of the 5-HT$_{1A}$ and 5-HT$_{1D}$ receptors. These compounds are useful in treating or preventing migraine, depression and other disorders for which a 5-HT$_1$ agonist or antagonist is indicated.

6 Claims, No Drawings

BENZYL(IDENE)-LACTAM DERIVATIVES, THEIR PREPARATION AND THEIR USE AS SELECTIVE (ANT) AGONISTS OF 5-HT$_{1A}$- AND/OR 5-HT$_{1D}$ RECEPTORS

This application is a division of Ser. No. 09/155,215, filed Sep. 24, 1998, now U.S. Pat. No. 6,462,048, which is a National Stage under 35 USC 371 of PCT/IB97/100076, filed Feb. 3, 1997, which claims the benefit of Ser. No. 60/015,134, filed Mar. 29. 1996.

BACKGROUND OF THE INVENTION

The present invention relates to lactam derivatives, to processes and intermediates for their preparation, to pharmaceutical compositions containing them and to their medicinal use. The compounds of the present invention include selective agonists and antagonists of serotonin 1 (5-HT$_1$) receptors, specifically, of one or both of the 5-HT$_{1A}$ and 5-HT$_{1D}$ receptors. They are useful in treating or preventing migraine, depression and other disorders for which a 5-HT$_1$ agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-HT$_1$ agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4substituted-1-piper-azinyl)-naphthalenes as useful 5-HT$_{1A}$ ligand therapeutics.

Glennon et al., refers to 7-methoxy-1-(1-piperazinyl)-naphthalene as a useful 5-HT$_1$ ligand in their article "5-HT$_{1D}$ Serotonin Receptors", *Clinical Drug Res. Dev.*, 22, 25–36 (1991).

Glennon's article "Serotonin Receptors: Clinical Implications", *Neuroscience and Behavoral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimers disease, Parkinsons disease and Huntingtons disease.

Ligands with high affinity for the 5-HT$_1$ receptors are well recognized as having therapeutic value for the treatment of human conditions caused by serotonin imbalance.

World Patent Application WO 95/31988, published Nov. 30, 1995, refers to the use of 5-HT$_{1D}$ antagonist in combination with a 5-HT$_{1A}$ antagonist to treat CNS disorders such depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction. G. Maura et al., *J. Neurochem*, 66 (1), pp 203–209 (1996), have stated that administration of agonists selective for 5-HT$_{1A}$ receptors or for both 5-HT$_{1A}$ and 5-HT$_{1D}$ receptors might represent a great improvement in the treatment of human cerebellar ataxias, a multifaceted syndrome for which no established therapy is available.

SUMMARY OF THE INVENTION

The present invention relates to compounds of the formula I, depicted below,

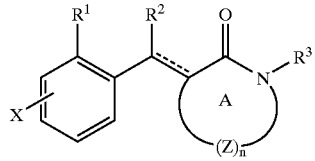

wherein R$^1$ is a group of the formula G$^1$, G$^2$, G$^3$, G$^4$ or G$^5$, depicted below,

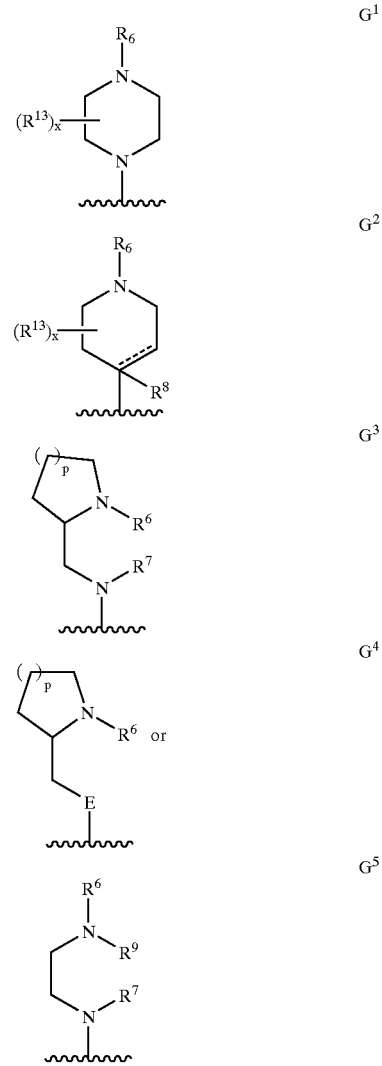

wherein E is oxygen, sulfur, SO or SO$_2$;

R$^6$ and R$^7$ are independently selected from hydrogen, (C$_1$–C$_5$) alkyl, [(C$_2$–C$_4$)alkyl]aryl wherein the aryl moiety is phenyl or naphthyl, and heteroaryl-(CH$_2$)$_q$ wherein the heteroaryl moiety is selected from pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents, preferably from zero to three substituents, independently selected from chloro, fluoro, bromo, iodo, (C$_1$–C$_6$)alkyl, (C$_1$–C$_6$)alkoxy, trifluoromethyl, cyano and $SO_g(C_1-C_6)$alkyl wherein g is zero, one or two;

or $R^6$ and $R^7$ together form a 2 to 4 carbon chain;

x is zero to eight;

each $R^{13}$ is, independently, $(C_1-C_4)$alkyl or a $(C_1-C_4)$ methylene bridge from one of the ring carbons of the piperazine or piperidine ring of $G^1$ or $G^2$, respectively, to the same or another ring carbon or a ring nitrogen of the piperizine or piperidine ring of $G^1$ or $G^2$, respectively, having an available bonding site, or to a ring carbon of $R^6$ having an available bonding site;

$R^8$ is selected from hydrogen and $(C_1-C_3)$ alkyl;

$R^9$ is selected from hydrogen and $(C_1-C_6)$alkyl;

or $R^6$ and $R^9$, together with the nitrogen atom to which they are attached, form a 5 to 7 membered ring;

and p is one, two, or three;

$R^2$ is hydrogen, $(C_1-C_4)$alkyl, phenyl or naphthyl, wherein said phenyl or naphthyl may optionally be substituted with one or more substituents, preferably from zero to three substituents, independently selected from chloro, fluoro, bromo, iodo, $(C_1-C_6)$alkyl, $(C_1-C_6)$alkoxy, trifluoromethyl, cyano and $SO_g(C_1-C_6)$alkyl wherein g is zero, one or two;

$R^3$ is $(CH_2)_mB$, wherein m is zero, one, two or three and B is hydrogen, phenyl, naphthyl or a 5 or 6 membered heteroaryl group containing from one to four hetero atoms in the ring (e.g., furyl, thienyl, pyridyl, pyrimidyl, thiazolyl, pyrazolyl, isothiazolyl, oxazolyl, isoxazolyl, pyrrolyl, triazolyl, tetrazolyl, imidazolyl, etc.), and wherein each of the foregoing aryl and heteroaryl groups may optionally be substituted with one or more substituents, preferably from zero to three substituents, independently selected from chloro, fluoro, bromo, iodo, $(C_1-C_6)$alkyl, $(C_1-C_6)$alkoxy, trifluoromethyl, cyano, hydroxy, COOH and $SO_g(C_1-C_6)$ alkyl wherein g is zero, one or two;

Z is $CR^4R^5$, wherein $R^4$ and $R^5$ are independently selected from hydrogen, $(C_1-C_6)$alkyl and trifluoromethyl; or Z may be one of the aryl or heteroaryl groups referred to in the definition of B above and wherein two adjacent ring members of Z are also members of ring A;

X is hydrogen, chloro, fluoro, bromo, iodo, cyano, $(C_1-C_6)$alkyl, hydroxy, trifluoromethyl, $(C_1-C_6)$alkoxy, $—SO_g(C_1-C_6)$alkyl wherein g is zero one or two, $CO_2R^{10}$ or $CONR^{11}R^{12}$;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered ring that may contain from zero to four heteroatoms selected from nitrogen, sulfur and oxygen, for example, where $NR^{11}R^{12}$ is pyrrolidinyl, pyrrolyl, imidazolyl, triazolyl, tetrazolyl, piperidyl, piperazinyl, morpholinyl, thiomorpholinyl, hexamethyleneiminyl, diazepinyl, oxazopinyl,thiazepinyl, oxadiazepinyl, thiadiazopinyl or triazepinyl;

n is one, two, three or four; and the broken line indicates an optional double bond;

with the proviso that n must be one when Z is an aryl or heteroaryl group;

and the pharmaceutically acceptable salts thereof.

The following are more specific embodiments of groups $G^1$ and $G^2$.

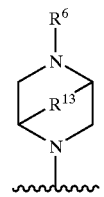

G¹-a

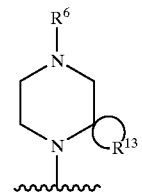

G¹-b

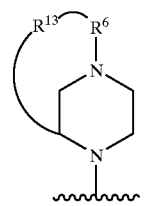

G¹-c

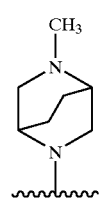

G¹-d

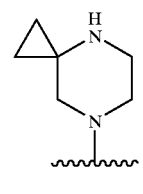

G¹-e

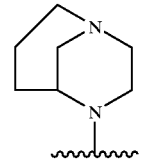

G¹-f

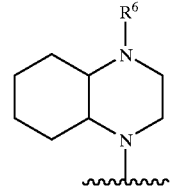

G¹-g

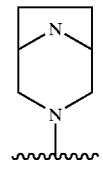

G¹-h

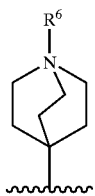

G²-a

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations e., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers and all optical isomers of compounds of the formula I (e.g., R and S enantiomers), as well as racemic, diastereomeric and other mixtures of such isomers.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine, bromine, and iodine.

Preferred compounds of the formula I include those wherein $R^1$ is piperazinyl.

Preferred compounds of the formula I also include those wherein Z is $CH_2$.

Preferred compounds of the formula I also include those wherein n is two or three.

Preferred compounds of the formula I also include those where in $R^3$ is substituted phenyl.

Examples of specific preferred compounds of the formula I are the following:

3-[2-(4-methylpiperazin-1-yl)-benzylidene]-1,3-dihydro-indol-2-one;
6-chloro-3-[2-(4-methylpiperazin-1-yl)-benzylidene]-1,3-dihydro-indol-2-one;
5-chloro-3-[2-(4-methylpiperazin-1-yl)-benzylidene]-1,3-dihydro-indol-2-one;
1-methyl-3-[2-(4-methylpiperazin-1-yl)-benzylidene]-1,3-dihydro-indol-2-one;
3-[2-(4-methylpiperazin-1-yl)-benzylidene]-1-phenyl-1,3-dihydro-indol-2-one;
1-(3,4-dichlorophenyl)-3-[2-(4-methylpiperazin-1-yl)-benzylidene]-pyrrolidin-2-one;
1-(3,4-dichlorobenzyl)-3-[2-(4-methylpiperazin-1-yl)-benzylidene]-1,3-dihydro-indol-2-one;
1-(4-chlorobenzyl)-3-[2-(4-methylpiperazin-1-yl)-benzylidene]-pyrrolidin-2-one;
1-(4-chlorobenzyl)-3-[5-fluoro-2-(4-methylpiperazin-1 yl)-benzylidene]-pyrrolidin-2-one;
1-(3,4-difluorophenyl)-3-[2-(4-methylpiperazin-1-yl)-benzylidene]-pyrrolidin-2-one;
1-(2,4-dichlorobenzyl)-3-[2-(4-methylpiperazin-1-yl)-benzylidene]-pyrrolidin-2-one;
1-(3,4-dichlorophenyl)-3-[5-fluoro-2-(4-methylpiperazin-1-yl)-benzylidene]-pyrrolidin-2-one;
1-(4-chlorobenzyl)-3-[2-(4-methylpiperazin-1-yl)-benzylidene]-piperidin-2-one;
1-(3,4-dichlorobenzyl)-3-[2-(4-methylpiperazin-1-yl)-benzylidene]-piperidin-2-one;
1-(4-chlorophenyl)-3-[5fluoro-2-(4methylpiperazin-1-yl)-benzylidene]-piperidin-2-one;
1-(3,4-dichlorophenyl)-3-[5-fluoro-2-(4-methylpiperazin-1-yl)-benzylidene]-piperidin-2-one;
3-[2-(4-methylpiperazin-1-yl)-benzylidene]-1-phenyl-pyrrolidin-2-one;
3-[2-(4-methylpiperazin-1-yl)-benzylidene]-1-(4-trifluoromethylphenyl)-pyrrolidin-2-one;
1-(3,4-difluorophenyl)-3-[2-(4-methylpiperazin-1-yl)-benzyl]-pyrrolidin-2-one;
3-[2-(4-methylpiperazin-1-yl)-benzylidene]-pyrrolidin-2-one;
3-[5-fluoro-2-(4-methylpiperazin-1-yl)-benzylidene]-pyrrolidin-2-one;
3-[2-(4-methylpiperazin-1-yl)-benzylidene]-piperidin-2-one;
1-(3,4-dichlorophenyl)-3-[2-(4-methylpiperazin-1-yl)-benzyl]-piperidin-2-one;
1-(4-methoxyphenyl)-3-[2-(4-methylpiperazin-1-yl)-benzylidene]-3,4-dihydro-1H-quinolin -2-one;
1-(3,4-dichlorophenyl)-3-[5-fluoro-2-(4-methylpiperazin-1-yl)-benzyl)-piperidin-2-one;
3-[2-(4-methylpiperazin-1-yl)-benzyl]-1-phenyl-pyrrolidin-2-one;
3-[2-(4-methylpiperazin-1-yl)-benzylidene]-1-(p-tolyl)-pyrrolidin-2-one;
3-[4-fluoro-2-(4-methylpiperazin-1-yl)-benzylidene]-1-phenyl-pyrrolidin-2-one;
1-(3,4-dichlorophenyl)-3-[2-fluoro-6-(4-methylpiperazin-1-yl)-benzylidene]-pyrrolidin-2-one;
1-(3,4-difluorophenyl)-3-[5-fluoro-2-(4methylpiperazin-1-yl)-benzylidene]-piperine -2-one;
1-[2-(4-chlorophenyl)ethyl]-3-[5-fluoro-2-(4methylpiperazin-1-yl)-benzylidene]-piperidin-2-one;
1-(3,4-dichlorophenyl)-3-[2-(2-dimethylaminoethoxy)-benzylidene]-pyrrolidin-2-one; and
3-[2-(4-methylpiperazin-1-yl)-benzyl]-1-(4-trifluoromethylphenyl)-pyrrolidin-2-one.

Other compounds of formula I include the following:
1-(3,4-dichlorophenyl)-3-[2-(4-methylpiperazin-1-yl)-benzylidene]-azetidin-2-one;
1-(3,4-dichlorophenyl)-3-[2-(4-methylpiperazin-1-yl)-benzylidene]-azepin-2-one;
1-(3,4-dichlorophenyl)-3-{1-[2-(4methylpiperazin-1-yl)phenyl]ethyl}-pyrrolidin-2-one;
1-(3,4-dichlorophenyl)-3-{1-[2-(4-methylpiperazin-1-yl)phenyl]ethyl-piperidine-2-one;
1-(3,4-dichlorophenyl)-3-{1-[2-(4-methylpiperazin-1-yl)phenyl]-ethylidene}-pyrrolidin-2-one;

1-(3,4-dichlorophenyl)-3-{1-[2-(4-methylpiperazin-1-yl) phenyl]-ethylidene}-piperidin-2-one;

1-(3,4-dichlorophenyl)-3-{[2-(4-methylpiperazin-1-yl) phenyl]-phenylmethylene}-pyrrolidin-2-one;

1-(3,4-dichlorophenyl)-3-{2-[(2-dimethylaminoethyl)-methylamino]-benzylidene}-pyrrolidin-2-one;

1-(3,4-dichlorophenyl)-3-[2-(pyrrolidin-1-ylethoxy)-benzylidene]-pyrrolidin-2-one;

1-(3,4-dichlorophenyl)-3-[2-(2-dimethylaminoethylamino)-benzylidene]-pyrrolidin-2-one;

2-(3,4-dichlorophenyl)-3-[2-(2-dimethylaminoethylamino)-benzylidene]-pyrrolidin -2-one;

2-(3,4-dichlorophenyl)-4-[2-(4-methylpiperazin-1-yl)-benzylidene]-octahydro-isoquinolin -3-one;

1-(3,4-dichlorophenyl)-3-[2-(4-methylpiperazin-1-yl)-benzylidene]-octahydro-quinolin -2one;

1-(3,4-dichlorophenyl)-3-[2-(4methylpiperazin-1-yl))-benzylidene]-octahydro-indol -2-one; and 1-(3,4-dichlorophenyl)-5,5-dimethyl-3-[2-(4methylpiperazin-1-yl)-benzylidene]-pyrrolidin-2-one.

The present invention also relates to a pharmaceutical composition for treating or preventing a disorder or condition selected from hypertension, depression, generalized anxiety disorder, phobias e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders involving changes in motility and secretion, and chronic paroxysmal hemicrania and headache associated with vascular disorders in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders involving changes in motility arid secretion, and chronic paroxysmal hemicrania and headache associated with vascular disorders in a mammal, preferably a human, comprising administering to a mammal in need of such treatment or prevention an amount of a compound of the formula I, or a pharmaceutically acceptable salt thereof, that Is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders involving changes in motility and secretion, and chronic paroxysmal hemicrania and headache associated with vascular disorders in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising a serotonin receptor antagonizing or agonizing effective amount of a compound of the formula I, or a pharmaceutically acceptable salt thereof, and a pharmaceutically acceptable carrier.

The present Invention also relates to a method for treating or preventing a disorder or condition selected from hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders involving changes in motility and secretion, and chronic paroxysmal hemicrania and headache associated with vascular disorders in a mammal, preferably a human, comprising administering to a mammal requiring such treatment or prevention a serotonin receptor antagonizing or agonizing effective amount of a compound of the formula I or a pharmaceutically acceptable salt thereof.

The present invention also relates to a method for treating or preventing a disorder or condition that can be treated or prevented by enhancing serotonergic neurotransmission in a mammal, preferably a human, comprising administering to a mammal requiring such treatment or prevention a serotonin receptor antagonizing or agonizing effective amount of a compound of the formula I or a pharmaceutically acceptable salt thereof.

The present invention relates to a pharmaceutical composition for treating or preventing a condition or disorder that can be treated or prevented by enhancing serotonergic neurotransmission in a mammal, preferably a human, comprising:

a) a pharmaceutically acceptable carrier;
b) a compound of the formula I or a pharmaceutically acceptable salt thereof; and
c) a 5-HT re-uptake inhibitor, preferably sertraline, or a pharmaceutically acceptable salt thereof;

wherein the amount of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal requiring such treatment or prevention:

a) a compound of the formula I, defined above, or a pharmaceutically acceptable salt thereof; and
b) a 5-HT re-uptake inhibitor, preferably sertraline, or a pharmaceutically acceptable salt thereof;

wherein the amounts of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to said mammal requiring such treatment or prevention:

a) a 5-HT$_{1A}$ antagonist or a pharmaceutically acceptable salt thereof; and
b) a 5-HT$_{1D}$ antagonist or a pharmaceutically acceptable salt thereof;

wherein the amounts of each active compound (i.e., the 5-HT$_{1A}$ antagonist and the 5-HT$_{1D}$ antagonist) are such that the combination is effective in treating or preventing such disorder or condition.

"Enhanced serotonergic neurotransmission," as used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

Sertraline, (1S-cis)-4-(3,4-dichlorophenyl)-1,2,3, 4tetrahydro-N-methyl-1-naphthalenamine, as used herein has the chemical formula $C_{17}H_{17}NCl_2$ and the following structural formula

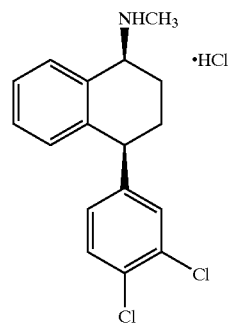

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

DETAILED DESCRIPTION OF THE INVENTION

Compounds of the formula I may be prepared according to the following reaction schemes and discussion. Unless otherwise indicated, $R^1$ through $R^{12}$, $G^1$ through $G^5$, X, A, B, E, Z, n, m, p, q, and g and structural formula I in the reaction schemes and discussion that follow are as defined above.

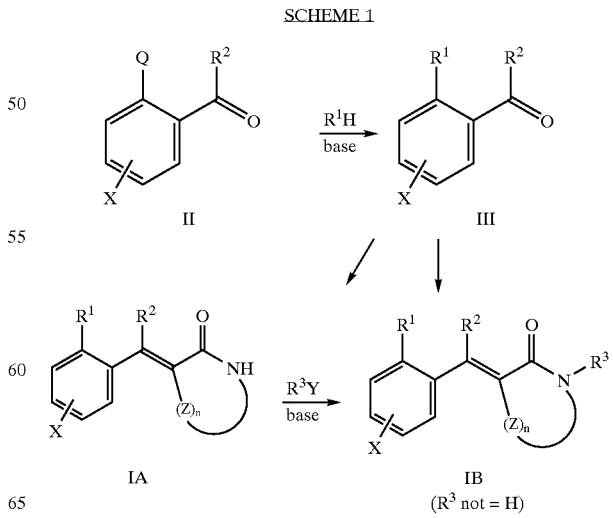

SCHEME 2

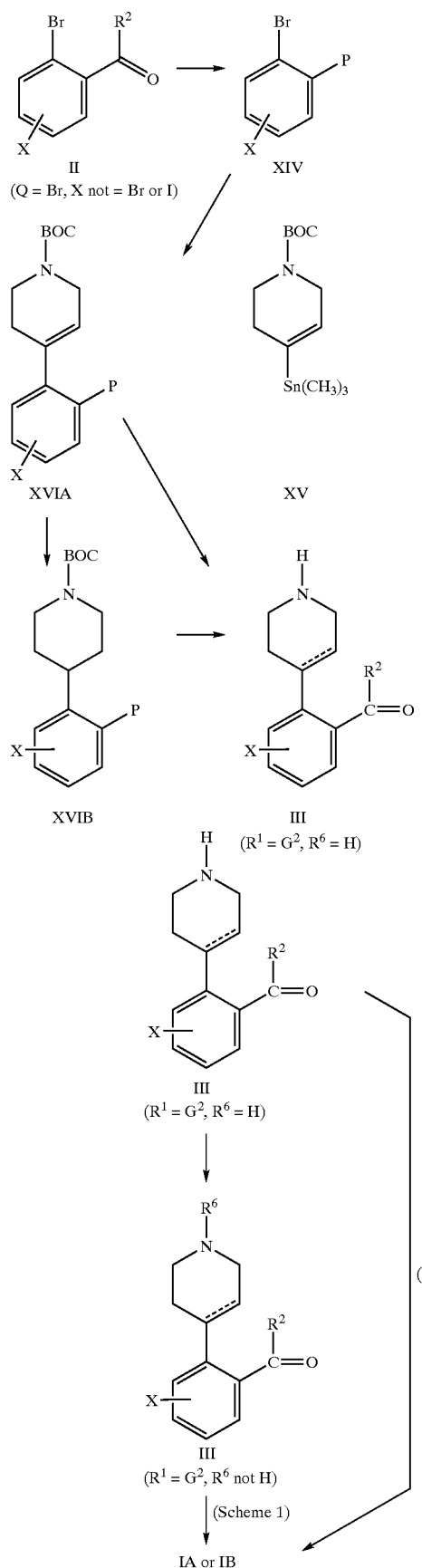

SCHEME 3

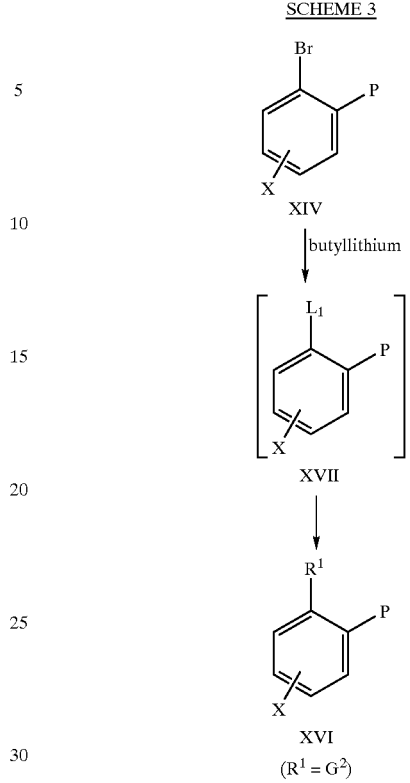

Scheme 1 illustrates a method of synthesizing compounds of the formula I wherein the dashed line represents a double carbon-carbon bond and $R^1$ is a group of the formula $G^1$, $G^3$, $G^4$ or $G^5$. Referring to Scheme 1, a compound of the formula II, wherein Q is a suitable leaving group (e.g., chloro, fluoro, bromo, mesylate, tosylate, etc.), is reacted with a compound of the formula $R^1H$, wherein $R^1$ is a group of the formula $G^1$, $G^3$, $G^4$ or $G^5$, in the presence of a base, to form the corresponding compound of formula III. This reaction is generally carried out at a temperature from about 0° C. to about 140° C., preferably at about the reflux temperature, in a polar solvent such as dimethyl sulfoxide (DMSO), N,N-dimethylformamide (DMF), N,N-dimethylacetamide (DMA) or N-methyl-2-pyrrolidinone (NMP), preferably DMF. Suitable bases include anhydrous sodium carbonate ($Na_2CO_3$), potassium carbonate ($K_2CO_3$), sodium hydroxide (NaOH) and potassium hydroxide (KOH), as well as tertiary amines such as pyrrolidine, triethylamine and pyridine. Anhydrous potassium carbonate is preferred.

Compounds of formula III can be converted into compounds of the formula I wherein $R^3$ is other than hydrogen (i.e., compounds of the formula IB, as depicted In Scheme 1), by subjecting them to an Aldol condensation or Wittig reaction. For example, in the case of an Aldol condensation, a compound of the formula III can be reacted with a compound of the formula

IV

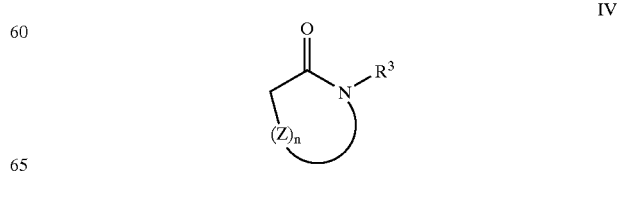

in the presence of a base, to form an aldol intermediate of the formula V, which may be isolated or converted directly in the same reaction step to a compound of the formula IB by the loss of water. The degree of completion for the conversion of compounds of the formula III to the aldol product of formula IB may be assessed using one or more analytical techniques, such as thin layer chromatography (tlc) or mass spectrometry. In some instances it may be possible or desirable to isolate the intermediate of formula V. In such case, the compound of formula V may be converted into the compound of formula IB by the elimination of water using techniques which are familiar to those skilled in the art, for example, by heating to the reflux temperature a solution of the compound of formula V in a solvent such as benzene, toluene or xylene, in the presence of a catalytic amount of benzene- or p-toluene-sulfonic acid with provision for the removal of the water generated. Such water removal techniques may involve the use of molecular sieves or a Dean-Stark trap to isolate the water created as an azeotrope with the solvent.

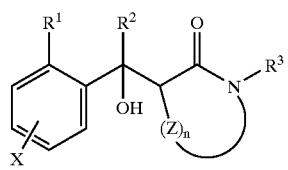

V

The aldol reaction is typically carried out in a polar solvent such as DMSO, DMF, tetrahydrofuran (THF), methanol or ethanol, at a temperature from about −25° C. to about 80° C. Preferably, this reaction is carried out in THF at about 25° C. Suitable bases for use in the aldol formation step include $K_2CO_3$, $Na_2CO_3$, sodium hydride (NaH), pyrrolidine and piperidine. Sodium hydride is preferred. Aldol condensations are described in "Modem Synthetic Reactions," Herbert O. House, 2d. Edition, W. A. Benjamin, Menlo Park, Calif. 1972, pp. 629–682.

Compounds of the formula I wherein $R^3$ is hydrogen (compounds of the formula IA, as depicted in Scheme 1) can be prepared via an Aldol condensation in a manner analogous to that described above for the formation of compounds of the formula IB, but using as the starting material a compound of the formula IV wherein $R^3$ is hydrogen or —C(=O)$R^{13}$ wherein $R^{13}$ is $(C_1-C_6)$alkyl or trifluoromethyl. Compounds of the formula IA may be converted into compounds of the formula IB by reacting them with a compound of the formula $R^3Y$ wherein Y is a leaving group and is defined as Q is defined as above. These reactions can be carried out In a solvent such as di-(alkyl)ether, THF, DMF, DMA or DMSO, preferably DMF, in the presence of a base such as potassium carbonate, sodium carbonate, sodium hydride, potassium hydride, sodium hydroxide or potassium hydroxide, preferably sodium hydride. Reaction temperatures can range from about 0° C. to about 150° C., preferably from about 25° C. to about the reflux temperature of the solvent.

Alternatively, the compound of formula IV can be converted into a compound of the formula IB by means of a Wittig olefination, as described in *Helvetica Chimica Acta.* 1963, 46, 1580 and depicted below.

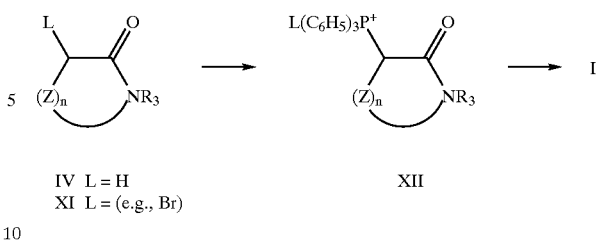

IV L = H
XI L = (e.g., Br)

XII

Thus, the compound of formula IV can be converted into the corresponding bromide of formula XI using standard bromination conditions, followed by treatment with triphenylphosphine in anhydrous THF to form the intermediate of formula XII. The compound of formula XII can then be treated with a strong base (e.g., aqueous $Na_2CO_3$) to generate the corresponding phosphonium ylide, which can then be reacted with the appropriate intermediate of formula III to produce compounds of general formula I. This transformation is described in A. Maercker, *Organic Reactions,* 1965, 14, 270.

Compounds of the formula I wherein the dashed line represents a single carbon-carbon bond may be prepared by hydrogenating the corresponding compounds wherein the dashed line represents a double carbon-carbon bond, using standard techniques that are well known to those skilled in the art. For example, reduction of the double bond may be effected with hydrogen gas ($H_2$), using catalysts such as palladium on carbon (Pd/C), palladium on barium sulfate (Pd/$Ba_2SO_4$), platinum on carbon (PVC), or tris(triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis,* Paul Rylander, Academic Press Inc., San Diego, 1979, pp. 31–63. The following conditions are preferred: Pd on carbon, methanol at 25° C. and 50 psi of hydrogen gas pressure. This method also provides for introduction of hydrogen isotopes (i.e., deuterium, tritium) by replacing $^1H_2$ with $^2H_2$ or $^3H_2$ in the above procedure.

An alternative procedure employing the use of reagents such as ammonium formate and Pd/C in methanol at the reflux temperature under an inert atmosphere (e.g., nitrogen or argon gas) is also effective in reducing the carbon-carbon double bond of compounds of the formula I. Another alternative method involves selective reduction of the carbon-carbon double bond using samarium and iodine or samarium iodide ($SmI_2$) in methanol or ethanol at about room temperature, as described by R. Yanada et. al., *Synlett.,* 1995, pp 443–4.

The starting materials of the formulas II and IV are either commercially available or known in the art. For example, compounds of formula II in which $R^2$ is hydrogen are readily available from commercial sources or may be prepared using procedures disclosed in the chemical literature. They may also be prepared from the corresponding carboxylic acids or esters (i.e., formula II wherein $R^2$=OH or O-alkyl), which are commercially available. These acids or esters can be reduced to the corresponding alcohols of formula XIII, depicted below, wherein Q is defined as for formula II, using one or more of a variety of reducing agents and conditions, depending upon the nature of the substituents Q and X.

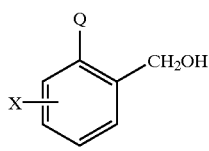

XIII

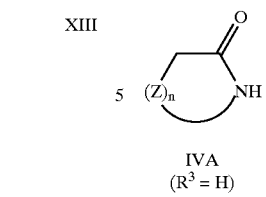

IVA
(R³ = H)

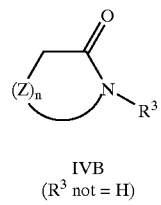

IVB
(R³ not = H)

Such reducing agents include sodium borohydride (NaBH₄), sodium cyanoborohydride (NaCNBH₃), lithium aluminum hydride (LiAlH₄) and borane in THF (BH₃·THF) in solvents such as methanol, ethanol, THF, diethyl ether and dioxane. Oxidation of the alcohol of formula XIII to the corresponding aldehyde of formula II may be accomplished using a selective oxidizing agent such as Jones reagent (hydrogen chromate (H₂CrO₄)), pyridinium chlorochromate (PCC) or manganese dioxide (MnO₂). References for such conversions are readily available (e.g. K. B. Wiberg, *Oxidation in Organic Chemistry, Part A*, Academic Press Inc, N.Y. 1965, pp. 69–72).

The starting materials of formula IV can be prepared by several methods, including procedures disclosed in the literature. For example, the compounds of formula IV wherein Z is an aromatic ring and n=1 (i.e., 1,3-dihydro-indol-2-one and substituted analogs thereof) are accessible commercially or may be prepared using methods disclosed in, e.g., H. R. Howard and R. Sarges, U.S. Pat. No. 4,476,307, Oct. 9, 1984. One method of preparing the starting materials of formula IV wherein Z is CR⁴R⁵ and n is one, two or three involves the condensation of a cyclic lactone of the formula VII with an amine of the formula H₂NR³, as shown below, in the presence of a strong mineral acid such as hydrochloric acid (HCl). (See M. J. Kornet, *J. Pharm. Sci.*, 1979, 68(3), 350; and *J. Het. Chem.*, 1966, 3, 311).

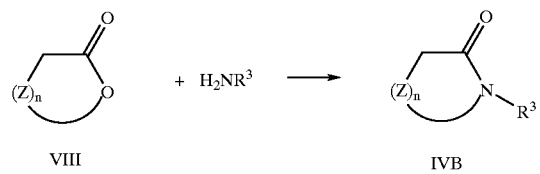

VIII → IVB

Alternatively, compounds of the formula IV wherein R³ is hydrogen (compounds of the formula IVA) may be alkylated to form the corresponding compounds wherein R³ is not hydrogen (compounds of the formula IB) using standard techniques available to those skilled in the art, e.g., by (a) generation of the anion of the desired compound of formula IVA using a strong base/polar solvent system such as NaH/THF, NaH/DMF or n-butyllithium/THF (n-buLi/THF), at a temperature from about −30° C. to about the reflux temperature of the solvent, for a period of about 5 minutes to about 24 hours, and (b) treatment of the anion with an alkylating agent of the formula R³Y wherein Y is a leaving group such as chloro, bromo, iodo or mesylate. This process Is depicted below.

The foregoing conversion of compounds of the formula IVA to those of the formula IVB may also be achieved using phase transfer catalysis conditions as described by Takahata et al., *Heterocycles*, 1979, 12(11), pp. 1449–1451.

The compounds of formula R¹H used in the preparation of intermediates of the formula III are readily available or may be prepared using standard methods of organic synthesis known to those skilled in the art and adapted from procedures disclosed in the chemical literature. For example, the preparation of compounds of the formula R¹H, wherein R¹ is G¹, may be accomplished using the following reaction sequence, beginning with commercially available N-tert-butoxycarbonyl piperazine (VI):

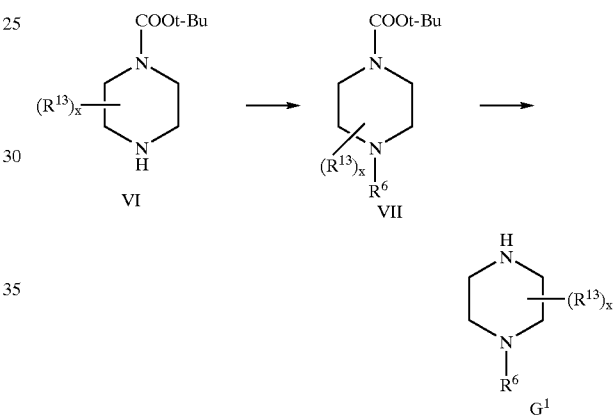

Alkylation of the compound of formula VI with a compound of the formula R⁶Y wherein Y is defined as above and R⁶ is (C₁–C₆)alkyl, aryl-(C₂–C₄)alkyl wherein the aryl moiety Is phenyl or naphthyl, or heteroaryl-(CH₂)_q, wherein q is zero, one, two, three or four, and the heteroaryl moiety is selected from pyridyl, pyrimidyl, benzoxazolyl, benzothiazolyl, benzisoxazolyl, and benzisothiazolyl, in the presence of an acid scavenger (e.g., sodium bicarbonate (NaHCO₃), potassium bicarbonate (KHCO₃), sodium carbonate (Na₂CO₃) or potassium carbonate (K₂CO₃)), in a polar solvent such as acetone at a temperature of about 10° C. to about the reflux temperature of the solvent, will yield the intermediate of formula VII. Removal of the tert-butoxy-carbonyl group can be accomplished using acidic conditions, e.g., HBr in acetic acid or trifluoroacetic acid until the reaction is judged to be complete.

Compounds of the formula III wherein R¹ is tetrahydropyridine or piperidine and R² is hydrogen can be prepared from 2-bromobenzaldehyde, which is commercially available, as depicted in Scheme 2. Referring to Scheme 2, the compound of formula II is first converted into a protected aldehyde or ketone of the formula XIV, wherein P represents the entire protected aldehyde or ketone moiety, using methods well known in the art. For example, the 1,3-dioxolane derivative of the aldehyde or ketone may be prepared according to the method described by J. E. Cole et al. *J.*

Chem. Soc., 1962, pp 244, by refluxing a solution of the aldehyde of formula II and 1,3-propanediol in anhydrous benzene with a catalytic amount of p-toluenesulfonic acid. When $R^2$ of formula II is not hydrogen, the ketone can be protected using an appropriate protecting group. Appropriate protecting groups can be chosen from many such groups based on the presence and nature of the substituent X. Examples of suitable protecting groups may be found in T. W. Greene, *Protecting Groups In Organic Synthesis*, John Wiley & Sons, New York, 1981. The most preferred protecting groups are those that are resistant to catalytic hydrogenation (e.g., 1,3-dioxolane), which would therefore allow for the subsequent reduction, if required, of the carbon-carbon double bond of the tetrahydropyridines of formula XVI.

Compounds of the formula XIV can then be treated with vinylstannanes of the formula XV, for example, 1-BOC-4-trimethylstannyl-1,2,5,6-tetrahydropyridine (BOC=tert-butyloxycarbonyl), in the presence of a catalyst, to form the corresponding compound of formula XVIA. Palladium is the preferred catalyst (for example, $(PH_3P)_4Pd$ or $Pd_2(dba)_3$), wherein dba=dibenzylideneacetone. This reaction may be carried out as described In "Palladium-catalyzed Vinylation of Organic Halides" In *Organic Reactions*, Vol 27, pp. 345–390, W. G. Dauben, Ed., John Wiley & Sons, Inc., New York, N.Y., 1982.

Compounds of formula III where $R^1$ is piperidine ($G^2$) can be prepared by catalytic hydrogenation of the tetrahydropyridine of formula XVIA from the previous paragraph using standard methods known in the art, generally using palladium on carbon as the catalyst, to form the corresponding compounds of formula XVIB. This reaction is typically performed in an inert solvent, such as ethanol or ethyl acetate, either with or without a protic acid such as acetic acid or HCl. Acetic acid is preferred. The protecting groups on $G^2$ (i.e., BOC) can be removed using one or more of the techniques described In Greene, referred to above, for example, stirring the compound of formula XVI in ethyl acetate and 3M hydrochloric acid at about room temperature for about 30 minutes. The protecting group for the aldehyde or ketone, P, can be converted into the unprotected ketone or aldehyde of the formula $—C(=O)R^2$ using one or more of the techniques described in Greene, for example, stirring a solution of the compound of formula XVI in THF and 5% hydrochloric acid at room temperature for 20 hours.

Compounds of the formula XIV from the previous reaction scheme may also be treated with alkyllithium reagents, for example butyllithium, sec-butyllithium or tert-butyllithium, preferably butyllithium in an inert solvent, as shown in Scheme 3, to form the intermediate lithium anion of formula XVII. Suitable solvents for this reaction include, for example, ether or tetrahydrofuran, preferably tetrahydrofuran. Reaction temperatures can range from about −110° C. to about 0° C. The intermediate lithium anions of formula XVII can then be further reacted with a suitable electrophile, selection of which depends on the presence and nature of the substituent. Suitable electrophiles for use in preparing compounds of the formula III wherein $R^1$ is a group of the formula $G^2$ include, for example, carbonyl derivatives or alkylating agents (e.g., 1-BOC-4-piperidone). In the case where an aldehyde or ketone is used as the electrophile, the hydroxy group must be removed from the intermediate of formula XVIII, as depicted below, in order to form the corresponding compound of formula III.

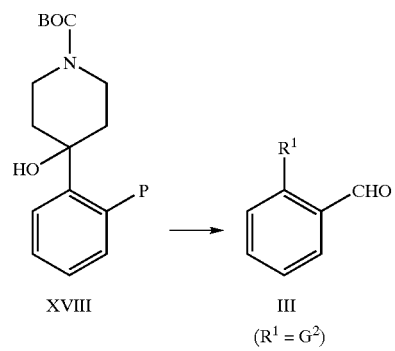

This step may be accomplished by one of several standard methods known in the art. For example, a thiocarbonyl derivative such as a xanthate may be prepared and removed by free radical processes, both of which are known to those skilled In the art. Alternatively, the hydroxyl group may be removed by reduction with a hydride source such as triethysilane under acidic conditions, using, for example, trifluoroacetic acid or boron trifluoride. The reduction reaction can be performed neat or in a solvent such as methylene chloride. A further alternative would be to first convert the hydroxyl group to a suitable leaving group, such as tosylate or chloride, using standard methods known in the art, and then to remove the leaving group with a nucleophilic hydride, such as, for example, lithium aluminum hydride. The latter reaction is typically performed in an inert solvent such as ether or tetrahydrofuran. Also, a reducing agent may be used to reductively remove the benzylic substituent. Suitable reducing agents include, for example, Raney nickel in ethanol and sodium or lithium in liquid ammonia. Another alternative method for removing the hydroxyl group is to first dehydrate the alcohol of formula XVIII to an olefin with a reagent such as Burgess salt (*J. Org. Chem.*, 1973, 38, 26) and then to catalytically hydrogenate the double bond under standard conditions with a catalyst such as palladium on carbon, The alcohol may also be dehydrated to the olefin by treatment with acid such as p-toluenesulfonic acid.

Compounds of the formula III wherein $R^1$ is $G^2$ and $R^6$ is hydrogen can be converted into the corresponding compounds of the formula III wherein $R^1$ is $G^2$ and $R^6$ is other than hydrogen by reacting them with a compound of the formula $R^6Y$, as described above for preparing compounds of the formula VII.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to Initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this Invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3naphthoate)] salts.

Those compounds of the formula I which are also acidic in nature, e.g., where $R^3$ includes a COOH or tetrazole moiety, are capable of forming base salts with various pharmacologically acceptable cations. Examples of such salts include the alkali metal or alkaline-earth metal salts and, particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are useful psychotherapeutics and are potent agonists and/or antagonists of the serotonin 1A ($5HT_{1A}$) and/or serotonin ID ($5\text{-}HT_{1D}$) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders involving changes in motility and secretion, and chronic paroxysmal hemicrania and headache associated with vascular disorders. These compounds are also useful as vasodilators.

The affinitie of the compounds of this invention for the various serotonin-1 receptors can be determined using standard radioligand binding assays as described in the literature. The $5HT_{1A}$ affinity can be measured using the procedure of Hoyer et al. (*Brain Res.,* 1986, 376, 85). The $5\text{-}HT_{1D}$ affinity can be measured using the procedure of Heuring and Peroutka (*J. Neurosci.,* 1987, 7, 894).

The in vitro activity of the compounds of the present invention at the $5\text{-}HT_{1D}$ binding site may be determined according to the following procedure. Bovine caudate tissue is homogenized and suspended in 20 volumes of a buffer containing 50 mM TRIS·hydrochloride (tris [hydroxymethyl]aminomethane hydrochloride) at a pH of 7.7. The homogenate is then centrifuged at 45,000G for 10 minutes. The supernatant is then discarded and the resulting pellet resuspended in approximately 20 volumes of 50 mM TRIS·hydrochloride (HCl) buffer at pH 7.7. This suspension is then pre-incubated for 15 minutes at 37° C., after which the suspension is centrifuged again at 45,000G for 10 minutes and the supernatant discarded. The resulting pellet (approximately 1 gram) is resuspended in 150 ml of a buffer of 15 mM TRIS·hydrochloride (HCl) containing 0.01 percent ascorbic acid with a final pH of 7.7 and also containing 10 μM pargyline and 4 mM calcium chloride ($CaCl_2$). The suspension is kept on ice at least 30 minutes prior to use.

The inhibitor, control or vehicle is then incubated according to the following procedure. To 50 μl of a 20 percent dimethylsulfoxide (DMSO)/80 percent distilled water solution is added 200 μl of tritiated 5-hydroxytryptamine (2 nM) in a buffer of 50 mM TRIS·hydrochloride containing 0.01 percent ascorbic acid at pH 7.7 and also containing 10 μM pargyline and 4 μM calcium chloride, plus 100 nM of 8-hydroxy-DPAT (dipropylaminotetraline) and 100 nM of mesulergine. To this mixture is added 750 μl of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters™). The pellet is then washed three times with 4 ml of a buffer of 50 mM TRIS·hydrochloride at pH 7.7. The pellet is then placed in a scintillation vial with 5 ml of scintillation fluid (aquasol 2 ™) and allowed to sit overnight. The percent inhibition can be calculated for each dose of the compound. An $IC_{50}$ value can then be calculated from the percent inhibition values.

The activity of the compounds of the present invention for $5\text{-}HT_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900G for 10 minutes and the supernate separated and recentrifuged at 70,000G for 15 minutes. The supernate is discarded and the pellet re-suspended in 10 volumes of 15 mM TRIS·hydrochloride at pH 7.5. The suspension is allowed to incubate for 15 minutes at 37° C. After pre-incubation is complete, the suspension is centrifuged at 70,000G for 15 minutes and the supernate discarded. The resulting tissue pellet is resuspended in a buffer of 50 mM TRIS·hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 μm pargyline and kept on ice.

The tissue is then incubated according to the following procedure. Fifty microliters of control, inhibitor, or vehicle (1 percent DMSO final concentration) is prepared at various dosages. To this solution is added 200 μl of tritiated DPAT at a concentration of 1.5 nM in a buffer of 50 mM TRIS·hydrochloride at pH 7.7 containing 4 mM calcium chloride, 0.01 percent ascorbic acid and pargyline. To this solution is then added 750 μl of tissue and the resulting suspension is vortexed to ensure homogeneity. The suspension is then incubated In a shaking water bath for 30 minutes at 37° C. The solution is then filtered, washed twice with 4 ml of 10 mM TRIS·hydrochloride at pH 7.5 containing 154 mM of sodium chloride. The percent inhibition is calculated for each dose of the compound, control or vehicle. $IC_{50}$ values are calculated from the percent inhibition values.

The compounds of formula I of the present Invention described in the following Examples were assayed for $5\text{-HT}_{1A}$ and $5\text{-HT}_{1D}$ affinity using the aforementioned procedures. All such compounds exhibited $IC_{50}$'s less than 0.60 $\mu$M for $5\text{-HT}_{1D}$ affinity and $IC_{50}$'s less than 1.0 $\mu$M for $5\text{-HT}_{1A}$ affinity.

The agonist and antagonist activities of the compounds of the invention at $5\text{-HT}_{1A}$ and $5\text{-HT}_{1D}$ receptors can be determined using a single saturating concentration according to the following procedure. Male Hartley guinea pigs are decapitated and $5\text{-HT}_{1A}$ receptors are dissected out of the hippocampus, while $5\text{HT}_{1D}$ receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000× g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM CAMP, 0.5 mM IBMX, 10 mM phosphocreatine, 0.31 mg/mL creatine phosphokinase, 100 $\mu$M GTP and 0.5–1 microcuries a$[^{32}P]$-ATP (30 Ci/mmol: NEG-003-New England Nuclear). Incubation is initiated by the addition of tissue to siliconized microfuge tubes (in triplicate) at 30° C. for 15 minutes. Each tube receives 20 $\mu$L tissue, 10 $\mu$L drug or buffer (at 10× final concentration), 10 $\mu$L 32 nM agonist or buffer (at 10× final concentration), 20 $\mu$L forskolin (3 $\mu$M final concentration) and 40 $\mu$L of the preceding reaction mix. Incubation is terminated by the addition of 100 $\mu$L 2% SDS, 1.3 mM CAMP, 45 mM ATP solution containing 40,000 dpm $[^{3}H]$-cAMP (30 Ci/mmol: NET-275-New England Nuclear) to monitor the recovery of CAMP from the columns. The separation of $[^{32}P]$-ATP and $[^{32}P]$-cAMP is accomplished using the method of Salomon et al., *Analytical Biochemistry*, 1974, 58, 541–548. Radioactivity is quantified by liquid scintillation counting. Maximal inhibition is defined by 10 $\mu$M (R)-8-OH-DPAT for $5\text{-HT}_{1A}$ receptors, and 320 nM B-HT for $5\text{-HT}_{1D}$ receptors. Percent inhibitions by the test compounds are then calculated in relation to the Inhibitory effect of (R)-8-OH-DPAT for $5\text{-HT}_{1A}$ receptors or 5-HT for $5\text{-HT}_{1D}$ receptors. The reversal of agonist Induced inhibition of forskolin-stimulated adenylate cyclase activity is calculated in relation to the 32 nM agonist effect.

The compounds of the Invention can be tested for in vivo activity for antagonism of $5\text{-HT}_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneous (s.c.) prior to the $5\text{-HT}_{1D}$ agonist, which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The $5\text{-HT}_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and $5\text{-HT}_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

Serotonin $5HT_1$ receptor affinity can be determined by the in vitro receptor binding assays, as described for the $5HT_{1A}$ receptor using rat cortex as the receptor source and $[^{3}H]$-8-OH-DPAT as the radioligand [D. Hoyer et al. *Eur. J. Pharm.*, 118, 13 (1985)] and as described for the $5\text{-HT}_{1D}$ receptor using bovine caudate as the receptor source and $[^{3}H]$ serotonin as the radioligand [R. E. Heuring and S. J. Peroutka, *J. Neuroscience*, 7, 894 (1987)]. Of the active compounds tested, all exhibited an $IC_{50}$ in either assay of 1 $\mu$M or less.

The compounds of formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, pheneizine or tranylcyclopramine) or 5HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5HT re-uptake inhibitor is referred herein to as "the active combinations"), are useful psychotherapeutics and may be used in the treatment or prevention of disorders the treatment or prevention of which is facilitated by enhanced serotonergic neurotransmission e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders (e.g., dementia, amnestic disorders, and age-associated memory impairment), Parkinson's diseases (e.g., dementia in Parkinson's disease, neuroleptic-induced Parkinsonism and tardive dyskinesias), endocrine disorders (e.g., hyperprolactinaemia), vasospasm (particularly in the cerebral vasculature), cerebellar ataxia, gastrointestinal tract disorders involving changes in motility and secretion and chronic paroxysmal hemicrania and headache associated with vascular disorders.

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described In Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsoft mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described In U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated In rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered In a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present In such dosage forms at concentration levels ranging from about 0.5% to about 90% by weight of the total composition, I.e., In amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention In the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 $\mu$g to about 1000 $\mu$g of the active compound of this invention, preferably from about 1 $\mu$g to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake Inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg. to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 $\mu$m silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

3-[2-(4-Methylpiperazin-1-yl)-benzylidene]-1,3-dihydro-indol-2-one

Under nitrogen in a dry round bottom flask fitted with a condensor and magnetic stir bar were placed 2-(4methyl-1-piperazinyl)-benzaldehyde (0.152 g, 0.75 g, 0.75 mmol), oxindole (0.104 g, 0.78 mmol) pyrrolidine (62 $\mu$L) and ethanol (7.0 mL). The mixture was heated to reflux for 16 hours, cooled and evaporated under reduced pressure. The residue was partitioned between ethyl acetate and water and the organic layer was washed with saturated aqueous sodium chloride (NaCl), dried over magnesium sulfate $(MgSO_4)_1$, filtered and absorbed onto 437 mg of silica gel. Elution with ethyl acetate (EtOAc) (125 mL), 1% methanol ($CH_3OH$) in EtOAc (100 mL), 2% $CH_3OH$ in EtOAc (100 mL) and 4% $CH_3OH$+1% triethylamine ($Et_3N$) In EtOAc (50 mL) gave 280 mg of a yellow solid. Recrystallization from hot $CH_3OH$ gave the title product, m.p. 226–2280° C.

$^1$H NMR ($CDCl_3$, 250 MHz) $\delta$ 7.93 (1H, s) 7.84 (1H, br s), 7.79 (1H, dd), 7.66 (1H, d, J=7.94 Hz), 7.42 (1H, dt), 7.12–7.03 (2H, m), 6.91–6.84 (2H, m), 3.06 (4H, t), 2.66–2.53 (4H, m), 2.35 (3H, s).

Elemental Analysis: Calc'd for $C_{20}H_{21}N_3O.0.5H_2O$: C, 73.15; H, 6.75; N, 12.79. Found: C, 73.00; H, 6.51; N, 13.01.

In the same manner the following analogs of Examples 2–6 were prepared:

EXAMPLE 2

6-Chloro-3-[2-(4-methlpiperazin-1-yl)-benzylidene]-1,3-dihydro-indol-2-one Hydrochloride Dihydrate m.p. 265–267° C.($CH_2Cl_2$).

PBMS: 354 ($M^+1$).

Elemental Analysis calc'd for $C_{20}H_{20}ClN_3O.HCl.2H_2O$: C, 56.34; H, 5.91; N, 9.86. Found: C, 56.83; H, 5.90; N, 10.07.

EXAMPLE 3

1-Methyl-3-[2-(4-methylpiperazin-1-yl)-benzylidene]-1,3-dihydro indol-2-one Hydrochloride Hydrate m.p. 120° C. decomp. ($Et_2O:CH_2Cl_2$).

PBMS: 334 ($M^{+1}$)

Elemental Analysis calc'd for $C_{21}H_{23}N_3O.HCl.2.5H_2O$: C, 60.79; H, 7.04; N, 10.13. Found: C, 61.04; H, 6.69; N, 10.18.

EXAMPLE 4

3-[2-(4-Methylpiperazin-1-yl)-benzylidene]-1-phenyl-1,3-dihydro-indol -2-one Hemihydrate m.p. 171–172° C. (EtOAc).
PBMS: 396 ($M^{+1}$).
Elemental Analysis calc'd for $C_{25}H_{25}N_3O.0.5\ H_2O$: C, 77.20; H, 6.48; N, 10.39. Found: C, 77.31; H, 6.43; N, 10.39.

EXAMPLE 5

1-(3,4-Dichlorobenzyl)-3-[2-(4methylpiperazin-1-yl)-benzyl -idene]-1,3-dihydro-indol-2-one.

m.p. 120–124° C. (EtOAc: Hexanes).
PBMS: 478 ($M^{+1}$).
Elemental Analysis calc'd for $C_{27}H_{25}Cl_2N_3O$: C, 67.78; H, 5.27; N, 8.78. Found: C, 67.85; H, 5.41; N, 8.53.

EXAMPLE 6

5-Chloro-3-[2-(4methylpiperazin-1-yl)-benzylidene]-1,3-dihydro-indol-2-one m.p. 235–2370° C. (MeOH).
PBMS 354 ($M^{+1}$).
Elemental Analysis calc'd for $C_{20}H_{20}ClN_3O$: C, 67.89; H, 5.70; N, 11.88. Found: C,67.39; H,5.67; N, 11.81.

EXAMPLE 7

1-(3,4-Dichlorophenyl)-3-[2-(4-methylpiperazin-1-yl)-benzylidene]-pyrrolidin-2-one hemidyrate Under nitrogen in a 3-necked flask fitted with a stirrer, thermometer and condenser were added 12.8 g (0.321 mol) of NaH (60% oil dispersion) and 2165 mL of anhydrous THF. After cooling to 0° C., a solution of 48.8 g (0.212 mol) of 1-(3,4-dichlorophenyl)-pyrrolidin-2-one and 42.7 g (0.209 mol) of 2-(4methyl-1-piperazinyl)-benzaldehyde in 1300 mL of THF was added with ice bath cooling. Following the addition, the mixture was heated at reflux for 7 hours, then concentrated in vacuo to a dark brown residue which was triturated with hot 10% EtOAc:hexanes. The remaining residue was filtered and air-dried to 95.6 g of a tan solid which was recrystallized from 16 L of MeOH to yield 24.2 g of an off-white solid. Additional recrystallization from $CHCl_3$:MeOH gave the title product as an off-white solid, 14.4 g, m.p. 224–225° C.

PBMS: 416 ($M^{+1}$), 418, 420
$^1$H-NMR ($CDCl_3$, 250 MHz) δ 7.98 (1H, d, J=2.6 Hz), 7.82 (1H, t, J=2.7 Hz), 7.70 (1H, dd), 7.48–7.41 (2H, m), 7.34 (1H, dt), 7.09 (2H, d, J=7.8 Hz). 3.91 (2H, t, J-6.8 Hz), 3.23–3.14 (2H, m), 3.00 (4H, sym m), 2.63 (4H, br s), 2.35 (3H, s).
Elemental Analysis: calc'd for $C_{22}H_{23}N_3OCl_2.0.5H_2O$: C, 62.12; H, 5.69; N, 9.88. Found: C, 62.06; H, 5.39; N, 9.69.

Additional crops of the title product were also isolated from the mother liquors retained from the recrystallizations.

The free base was converted to the hydrochloride salt by dissolving the base in methanol and add 1 N HCl in $Et_2O$ to precipitate the salt which was recrystallized from methanol: $Et_2O$ to a white crystalline solid, m.p. 177–179° C.
Elemental Analysis calc'd. for $C_{22}H_{23}N_3OCl_2.HCl.1.5H_2O$: C, 55.07; H, 5.67; N, 8.76. Found: C, 55.22; H, 5.61; N, 8.73.

By the same procedure, the following compounds of Examples 8–28 were also prepared:

EXAMPLE 8

1-(2.4-Dichlorophenyl)-3-[2-(4-methylpiperazin-1-yl)-benzylidene]pyrrolidin-2-one m.p. 228–229° C.
PBMS: 416 ($M^{+1}$).
Elemental Analysis calc'd for $C_{22}H_{23}N_3OCl_2$: C, 63.47; H, 5.57; N, 10.09. Found: C, 63.30; H, 5.53; N, 10.12.

EXAMPLE 9

1-(3,4-Difluorophenyl)-3-[2-(4-methylpiperazin-1-yl)-benzylidene]-pyrrolidin-2-one m.p. 228–229° C.
PBMS: 384 ($M^{+1}$).
Elemental Analysis calc'd for $C_{22}H_{23}FN_3O.\frac{1}{3}H_2O$: C, 67.85; H, 6.13; N, 10.79. Found: C, 67.99; H, 6.02; N, 10.86.

EXAMPLE 10

1-(3,4Dichlorophenyl)-3-[5-fluoro-2-(4-methylpiperazin-1-yl)-benzylidene]-pyrrolidin-2-one hemihydate m.p. 228–229° C.
PBMS: 434 ($M^{+1}$).
Elemental Analysis calc'd for $C_{22}H_{22}Cl_2FN_3O.0.5H_2O$: C, 59.60; H, 5.23; N, 9.48. Found: C, 59.67; H, 5.02; N, 9.44.

EXAMPLE 11

1-(4Chlorophenyl)-3-[2-(4-methylpiperazin-1-yl)-benzylidene]-piperidin-2-one m.p. 177–178° C. (EtOAc).
PBMS: 396 ($M^{+1}$).

EXAMPLE 12

1-(3,4-Dichlorophenyl)-3-[2-(4-methylpiperazin-1-yl)-benzylidene]-piperidin-2-one m.p. 138–139.5° C. (EtOAc).
PBMS: 430 ($M^{+1}$).

EXAMPLE 13

1-(4-Chlorophenyl)-3-[5-fluoro-2-(4-methylpiperazin-1-yl)-benzylidene]-piperidin-2-one m.p. 158–159° C. ($Et_2O$).
PBMS: 414 ($M^{+1}$).

EXAMPLE 14

1-(3,4-Dichlorophenyl)-3-[5-fluoro-2-(4methylpiperazin-1-yl)-benzylidene]-piperidin-2-one m.p. 161–162° C. (EtOAc)
PBMS: 448 ($M^{+1}$).

EXAMPLE 15

3-[2-(4-Methylpiperazin-1-yl)-benzylidene]-1 phenylpyrrolidin-2-one m.p. 178–179.5° C.
PBMS: 348 ($M^{+1}$).
Elemental Analysis calc'd for $C_{22}H_{25}N_3O$: C, 76.05; H, 7.25; N, 12.09. Found: C, 76.36; H, 6.90; N, 12.18.

EXAMPLE 16

3-[2-(4-Methylpiperazin-1-yl)-benzylidene]-1-(4-trifluoromethylphenyl)-pyrrolidin-2-one m.p. 185–186.5° C.
PBMS: 416 ($M^{+1}$).
Elemental Analysis calc'd for $C_{23}H_{24}F_3N_3O$: C, 66.49; H, 5.82; N, 10.11. Found: C, 66.42; H, 5.85; N, 10.18.

EXAMPLE 17

3-[2-(4-Methylpiperazin-1-yl)-benzylidene]-1-tolyl-pyrrolidin-2-one m.p. 165–167° C.
PBMS: 362 ($M^{+1}$).
Elemental Analysis calc'd for $C_{23}H_{27}N_3O \cdot 0.25H_2O$: C, 75.48; H, 7.57; N, 11.48. Found: C, 75.68; H, 7.56; N, 11.39.

EXAMPLE 18

1-(4-Chlorophenyl)-3-[2-(4-methylpiperazin-1-yl)-benzylidene]-pyrrolidin-2-one m.p. 188–190° C.
PBMS: 382 ($M^{+1}$).
Elemental Analysis calc'd for $C_{22}H_{24}ClN_3O \cdot 0.25 C_4H_8O_2$: C, 68.39; H, 6.49; N, 10.40. Found: C, 68.24; H, 6.62; N 10.18.
(compound contained ¼ mole of ethyl acetate)

EXAMPLE 19

3-[4Fluoro-2-(4-methylpiperazin-1-yl)-benzylidene]-1-phenylpyrrolidin-2-one m.p. 199–200.5° C.
PBMS: 366 ($M^{+1}$).

EXAMPLE 20

1-(3,4-Dichlorophenyl)-3-[2-fluoro-6-(4-methylpiperazin-1-yl)-benzylidene]-pyrrolidin-2-one m.p. 170–171° C.
PBMS: 434 ($M^{+1}$).
Elemental Analysis calc'd for $C_{22}H_{22}Cl_2FN_3O$: C, 60.84; H, 5.11; N, 9.67. Found: C, 60.77; H, 5.07; N, 9.62.

EXAMPLE 21

1-(3,4-Difluorophenyl)-3-[5-fluoro-2(4-methylpiperazin-1-yl)-benzylidene]-piperidin-2-one m.p. 168–170° C. (MeOH:$Et_2O$).
PBMS: 416 ($M^{+1}$).

EXAMPLE 22

1-[2-(4Chlorophenyl)ethyl]-3-[5-fluoro-2-(4-methylpiperazin-1-yl)-benzylidene]-piperidin-2-one m.p. 88–90° C. ($Et_2O$).
PBMS: 442 ($M^{+1}$).

EXAMPLE 23

1-(4-Chlorobenzyl)-3-[2-(4-methylpiperazin-1-yl)-benzylidene]-pyrrolidin-2-one m.p. 129–130° C.
PBMS: 396 ($M^{+1}$).

EXAMPLE 24

1-(4-Chlorobenzyl)-3-[5-fluoro-2-(4-methylpiperazin-1-yl)-benzylidene]-pyrrolidin-2one m.p. 131–132° C.
PBMS: 414 ($M^{+1}$).

EXAMPLE 25

1-(3,4-Dichlorobenzyl)-3-[2-(4-methylpiperazin-1-yl)-benzyl]-idene]-pyrrolidin-2-one m.p. 118–119° C.
PBMS: 430 ($M^{+1}$).
Elemental Analysis calc'd for $C_{23}H_{25}Cl_2N_3O \cdot 0.25H_2O$: C, 63.52; H, 5.91; N, 9.66. Found: C, 63.38; H, 5.85; N, 9.67.

EXAMPLE 26

1-(3,4-Dichlorobenzyl)-3-[2-(4-methylpiperazin-1-yl)-benzylidene]-piperidin-2-one

PBMS: 444 ($M^{+1}$).

EXAMPLE 27

1-(3,4-Dichlorophenyl)-3-[2-(2-dimethylaminoethoxy)-benzylidene]-pyrrolidin-2one m.p. 111–112° C. (free base), 241–242° C. (HCl salt).
PBMS: 405 ($M^{+1}$).
Elemental Analysis calc'd for $C_{21}H_{22}Cl_2N_2O_2$: C, 62.23; H, 5.47; N, 6.91. Found: C, 62.42; H, 5.46; N, 6.86.

EXAMPLE 28

1-(3,4-Dichlorophenyl)-3-[5-methyl-2-(4-methylpiperazin-1-yl)-benzylidene]-pyrrolidin-2one m.p. 149–150° C.
PBMS: 430 ($M^{+1}$).

EXAMPLE 29

1-(3,4-Difluorophenyl)-3-[2-(4-methylpiperazin-1-yl)-benzyl]-pyrrolidin-2-one

A mixture of 1-(3,4-difluorophenyl)-3-[2-(4-methylpiperazin-1-yl)-benzylidene]-pyrrolidin-2-one (125 mg, 0.326 mmol), ammonium formate (411 mg, 6.53 mmol) and 10% palladium on carbon (40 mg) in 30 mL of anhydrous methanol was refluxed under nitrogen for 18 hours. After cooling, the catalyst was removed In vacuo and the residue was treated with saturated aqueous sodium bicarbonate and methylene chloride. The organic layer was removed, combined with a second extraction of the aqueous layer with additional methylene chloride, washed with saturated aqueous sodium chloride (NaCl) and dried. The solvent was again removed In vacuo to give the crude product as a white solid (111 mg). This solid was dissolved in hot ethyl acetate and crystallized by the addition of a few drops of hexanes. The title product, 29 mg, has m.p. 130-131° C. From the filtrate a second crop of product was also obtained as above, 50 mg, mp. 130–131° C.

Mass spectrum: 386 ($M^{+1}$).

$^1$H-NMR (CDCl$_3$, 250 MHz) δ 7.75 (1H, m), 7.33–7.00 (6H, m), 3.71–3.60 (2H, m) 3.39 (1H, dd, J=13.5, 4.2 Hz), 3.08 (1H, m), 2.93 (4H, dd, J=8.8, 4.2 Hz), 2.78 (1H, dd, J=13.5, 10.2 Hz), 2.59 (4H, br s), 2.36 (3H, s), 2.17–2.01 (1H, m), 1.94–1.76 (1H, m).

Elemental Analysis: Calc'd for $C_{22}H_{25}F_2N_3O$: C, 68.55; H, 6.54; N, 10.90. Found: C, 68.55; H, 6.53; N, 10.90.

EXAMPLE 30

3-[2-(4-Methylpiperazin-1-yl)-benzyl]-1-phenyl-pyrrolidin-2-one

In a manner similar to the procedure of Example 29, 3-[2-(4methylpiperazin-1-yl)-benzylidene]-1-phenyl-pyrrolidin-2-one was converted to 3-[2-(4-methylpiperazin-1-yl)-benzyl]-1-phenyl-pyrrolidin-2-one, m.p. 104–105.5° C.

Mass spectrum: 350 ($M^{+1}$).

$^1$H-NMR (CDCl$_3$, 250 MHz) δ 7.68 (2H, dd, J=8.7, 1.1 Hz), 7.39 (2H, t), 7.26–7.03 (5H, m), 3.76–3.69 (2H, m), 3.40 (1H, dd, J=13.5, 3.9 Hz), 3.06 (1H, m), 2.96 (4H, dd, J=5.2, 3.5 Hz), 2.81 (1H, dd, J=13.5, 3.9 Hz), 2.59 (4H, br s), 2.36 (3H, s), 2.16–2.00 (1H, m), 1.94–1.76 (1H, m).

EXAMPLE 31

3-[2-(4-methylpiperazin-1-yl)-benzyl]-1-(4-trifluoromethyl-phenyl)-pyrrolidin-2-one Hydrochloride hemihydrate 3-[2-(4-methylpiperazin-1-yl)-benzylidene]-1-(4-trifluoromethylphenyl)-pyrrolidin-2-one was converted to 3-[2-(4methylpiperazin-1-yl)-benzyl]-1-(4-trifluoromethylphenyl)-pyrrolidin -2-one hydrochloride hemihydrate, m.p. 181–183° C.

Mass spectrum: 418 ($M^{+1}$).

$^1$H-NMR (DMSO-d$_6$, 250 MHz) δ 10.61 (1H, br s), 7.91 (2H, d, J=8.5 Hz) 7.72 (2H, d, J=8.9 Hz), 7.307.18 (2H, m), 7.18–7.03 (2H, m), 3.73 (2H, t, J=6.7 Hz), 3.50–3.33 (2H, m), 3.22–2.94 (8H, m), 2.78 (3H, s), 2.70 (1H, dd, J=13.7, 10.2 Hz), 2.03 (1H, m), 1.74 (1H, m).

Elemental Analysis: Calc'd for $C_{23}H_{26}N_3OF_3 \cdot HCl \cdot \frac{1}{2}H_2O$: C, 59.67, H, 6.10, N, 9.08. Found: C, 59.84; H, 6.06; N, 8.96.

EXAMPLE 32

1-[3,4Dichlorophenyl)-3-[2-(4-methylpiperazin-1-yl)-benzyl]-piperidin-2-one Hydrochloride A solution of 1-(3,4-dichlorophenyl)-3-[2-(4-methylpiperazin-1-yl)-benzylidene]-piperidin-2-one (260 mg, 0.60 mmol) in 20 mL of methanol was combined with 100 mg of 10% palladium on carbon and hydrogenated on a Parr Shaker apparatus at 50 psi for a total of 4 hours. The catalyst was then removed by filtration though diatomaceous earth and the solvent was removed in vacuo to give a yellow gummy residue. Chromatography (silica gel) eluting with 5% methanol (CH$_3$OH)/95% methylene chloride (CH$_2$Cl$_2$) gave clean product, 70 mg, as a clear gum which was dissolved in dry ethyl ether (Et$_2$O) and treated with HCl saturated ethyl ether to produce the hydrochloride salt, 61 mg, m.p. 106–108° C.

Mass spectrum: 432 ($M^{+1}$), 434.

EXAMPLE 33

1-[3,4-Dichlorophenyl)-3-[5-fluoro-2-(4-methylpiperazin-1-yl)-benzyl]-piperidin-2-one Hydrochloride Using a procedure similar to that of Example 32, 1-(3,4-dichlorophenyl)-3[5fluoro-2-(4-methylpiperazin-1-yl)-benzylidene]-piperidin-2-one (270 mg, 0.6 mmol) was reduced after 18 hours to give, after conversion to the hydrochloride salt, 1-[3,4-dichlorophenyl)-3-[5-fluoro-2-(4-methylpiperazin-1-yl)-benzyl]-piperidin-2-one hydrochloride, m.p. 83–85° C., white solid.

Mass spectrum: 450 ($M^{+1}$), 452.

What is claimed is:

1. A compound of the formula I, depicted below,

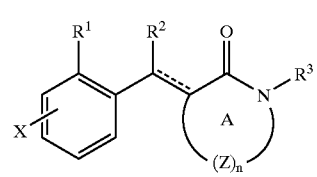

(I)

wherein $R^1$ is a group of the formula $G^1$, depicted below,

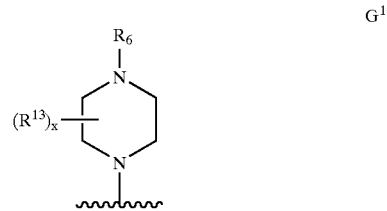

$G^1$ wherein $R^6$ independently selected from hydrogen, ($C_1$–$C_8$) alkyl, [($C_2$–$C_4$)alkyl]aryl wherein the aryl moiety is phenyl or naphthyl, and wherein said aryl moiety may optionally be substituted with one or more substituents independently selected from chloro, fluoro, bromo, iodo, ($C_1$–$C_6$)alkyl, ($C_1$–$C_8$)alkoxy, trifluoromethyl, cyano and $SO_g$($C_1$–$C_5$)alkyl wherein g is zero, one or two;

x is zero to eight;

each $R^{13}$ is, independently, ($C_1$–$C_4$)alkyl;

$R^2$ is hydrogen, ($C_1$–$C_4$)alkyl, phenyl or naphthyl, wherein said phenyl or naphthyl may optionally be sustituted with one or more substituents independently selected from chloro, fluoro, brom, iodo, ($C_1$–$C_8$)alkyl, ($C_1$–$C_8$)alkoxy, trifuoromethyl, cyano and $SO_g$($C_1$–$C_6$) alkyl wherein g is zero, one or two;

$R^3$ is $(CH_2)_mB$, wherein m is zero, one, two or three and B is hydrogen, phenyl or naphthyl and wherein each of the foregoing phenyl and naphthyl groups may optionally be substituted with one or more substituents independently selected from chloro, fluoro, bromo, iodo, ($C_1$–$C_6$)alkyl, ($C_1$–$C_6$)alkoxy, trifluoromethyl, cyano hydroxy, COOH and $SO_g$($C_1$–$C_6$)alkyl wherein g is zero, one or two;

Z is $CR^4R^5$, wherein $R^4$ and $R^5$ are independently selected from hydrogen, ($C_1$–$C_6$)alkyl and trifluoromethyl; or Z is a combination one $CR^4R^5$ and a phenylene or naphthylene wherein two adjacent ring members of said phenylene or naphthylene are also members of ring A;

X is hydrogen, chloro, fluoro, bromo, iodo, cyano, ($C_1$–$C_6$)alkyl, hydroxy, trifluoromethyl, ($C_1$–$C_6$) alkoxy, —$SO_g$($C_1$–$C_6$)alkyl wherein g is zero one or two, $CO_2R^{10}$ or $CONR^{11}R^{12}$;

each of $R^{10}$, $R^{11}$ and $R^{12}$ is selected, independently, from the radicals set forth in the definition of $R^2$;

n is three; and the broken line indicates an optional double bond;

with the proviso that when Z is a combination of one $CR^4R^5$ and a phenylene or naphthylene wherein two adjacent ring members of said phenylene or naphtylene are also members of ring A then n is 1;

or a pharmaceutically acceptable salt thereof.

2. A compound according to claim 1 wherein Z is $CH_2$.

3. A compound according to claim 1, wherein $R^3$ is substituted phenyl.

4. A compound according to claim 1, wherein said compound is selected from:

1-(4-chlorobenzyl)-3-[2-(4methylpiperazin-1-yl)-benzylidene]-piperidin-2-one;

1-(3,4-dichlorobenzyl)-3-[2-(4-methylpiperazin-1-yl)-benzylidene]-piperidin-2-one;

1-(4-chlorophenyl)-3-[5-fluoro-2-(4-methylpiperazin-1-yl)-benzylidene]-piperidin-2-one;

1-(3,4-dichlorophenyl)-3-[5-fluoro-2-(4-methylpiperazin-1-yl)-benzylidene]-piperidin-2-one;

3-[2-(4-methylpiperazin-1-yl)-benzylidene]-piperidin-2-one;

1-(3,4-dichlorophenyl)-3-[2-(4methylpiperazin-1-yl)-benzyl]-piperdin-2-one;

1-(4-methoxyphenyl)-3-[2-(4-methylpiperazin-1-yl)-benzylidene]-3,4dihydro-1H-quinolin-2-one;

1-(3,4-dichlorophenyl)-3-[5-fluoro-2-(4methylpiperazin-1-yl)-benzyl]-piperdin-2one;

1-(3,4-difluorophenyl)-3-[5-fluoro-2-(4-methylpiperazin-1-yl)-benzylidene]-piperidin-2-one;

1-[2-(4-chlorophenyl)ethyl]-3-[5-fluoro-2-(4-methylpiperazin-1-yl)-benzylidene]-piperdin-2-one;

and the pharmaceutically acceptable salts of such compounds.

5. A pharmaceutical composition for treating or preventing a disorder or condition selected from depression, generalized anxiety disorder, phobias, posttraumatic stress syndrome, obsessive-compulsive disorder, and panic disorder in a mammal, comprising an amount of a compound according to claim 1 that is effective in treating or preventing such disorder or condition and a pharmaceutically acceptable carrier.

6. A method for treating or preventing a disorder or condition selected from depression, generalized anxiety disorder, phobias, posttraumatic stress syndrome, obsessive-compulsive disorder, and panic disorder in a mammal, comprising administering to a mammal in need of such treatment or prevention an amount of a compound according to claim 1 that is effective in treating or preventing such disorder or condition.

* * * * *